United States Patent [19]

Hopper

[11] Patent Number: 4,727,105
[45] Date of Patent: Feb. 23, 1988

[54] OLIGOMERIC AMINE AND PHENOLIC ANTIDEGRADANTS

[75] Inventor: Roger J. Hopper, Akron, Ohio

[73] Assignee: The Goodyear Tire & Rubber Company, Akron, Ohio

[21] Appl. No.: 605,035

[22] Filed: Jan. 25, 1985

[51] Int. Cl.$^4$ .................. C07C 149/43; C07C 149/42; C07C 149/32; C08K 5/36
[52] U.S. Cl. ...................... 524/217; 524/239; 524/332; 560/18; 564/154; 568/22; 568/26
[58] Field of Search ............... 524/331, 217, 239, 240, 524/332, 368; 564/154; 560/18; 568/22, 26

[56] References Cited

U.S. PATENT DOCUMENTS

| | | | |
|---|---|---|---|
| 3,167,527 | 1/1965 | Hechenbleikne et al. | 524/181 |
| 3,330,804 | 7/1967 | O'Shea | 524/331 |
| 3,975,414 | 8/1976 | Kline | 524/217 |

Primary Examiner—Veronica P. Hoke
Attorney, Agent, or Firm—M. R. Dion, Sr.

[57] ABSTRACT

There is disclosed a compound having the structure

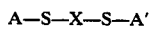

A—S—X—S—A'     I wherein A and A' are radicals independently selected from the group consisting of the following structures:

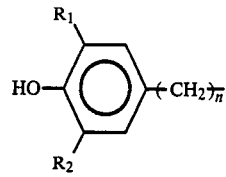

II

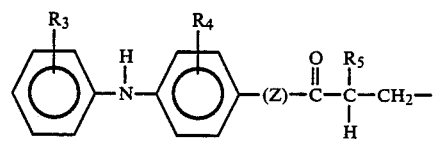

III wherein $R_1$ and $R_2$ are tertiary alkyl radicals having 4 to 8, preferably 4 to 6 carbon atoms, n is a whole number of 1 to 8, $R_3$ and $R_4$ are the same or different radicals selected from the group consisting of hydrogen and alkyl radicals having 1 to 18 carbon atoms, $R_5$ is hydrogen or methyl and Z is —O— or

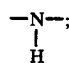

A' can also be hydrogen; and X is a divalent oligomeric segmer having the structure:

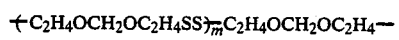

IV wherein m ranges from an average of 4 to about 24.

There is also disclosed a polymeric cmposition comprising a polymer susceptible to the degradative effects of oxidation having incorporated therein an antidegradant amount of a compound of Structure I.

14 Claims, No Drawings

OLIGOMERIC AMINE AND PHENOLIC ANTIDEGRADANTS

TECHNICAL FIELD

This invention relates to antidegradants. More particularly it relates to antidegradants and their use in protecting polymers and rubber compounds from the degradative effects of oxidation.

BACKGROUND ART

Essentially all types of rubber, both natural and synthetic, and particularly rubbers formed from dienes are known to be susceptible to deterioration resulting from prolonged exposure to oxygen, ozone, light and heat. A great deal of effort has been expended by those engaged in the field of polymer technology to develop various antidegradants that will effectively inhibit the adverse effects of aging of polymeric compositions. In addition, much work has been done to discover new ways to prevent antidegradants from leaving polymer compositions by extraction, migration or volatilization. One particular area of concern deals with the antidegradants used in the tire industry where improvements in the tires have increased their serviceable life thus prolonging the exposure to the degradative effects mentioned above.

One approach to the problems of extraction and volatilization has been to use compounds of higher molecular weight such as those disclosed in U.S. Pat. Nos. 3,975,414 and 4,152,319. Another approach has been to use a polymerizable antidegradative monomer to form polymers containing the segmeric form of the monomer as an integral part thereof. Such an approach is disclosed in U.S. Pat. Nos. 3,658,769 and 3,817,916. Still another approach has been to graft a reactive antidegradant onto an existing polymer chain as disclosed in U.S. Pat. No. 4,155,955.

The focus in the latter two approaches has been on polymers of high molecular weights. High molecular weight polymer-bound antidegradants can have a limited range of application due to their mutual insolubility or incompatability with dissimilar polymers. In addition, antidegradant monomers can not be incorporated in those polymers where the antidegradant functionality destroys the polymerization catalysts.

DISCLOSURE OF THE INVENTION

In accordance with the practice of the present invention, there is disclosed a compound having the structure $$A-S-X-S-A' \qquad \text{I}$$

wherein A and A' are radicals independently selected from the group consisting of the following structures:

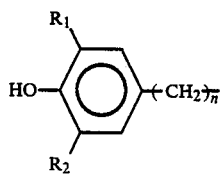

II and

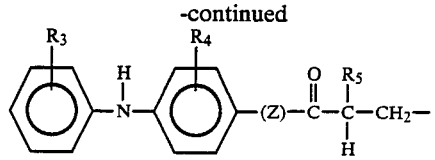

III wherein $R_1$ and $R_2$ are tertiary alkyl radicals having 4 to 8, preferably 4 to 6 carbon atoms, n is a whole number of 1 to 8, $R_3$ and $R_4$ are the same or different radicals selected from the group consisting of hydrogen and alkyl radicals having 1 to 18 carbon atoms, $R_5$ is hydrogen or methyl and Z is —O— or

A' can also be hydrogen; and X is a divalent oligomeric segmer having the structure:

IV wherein m ranges from an average of 4 to about 24.

There is also disclosed a polymeric composition comprising a polymer susceptible to the degradative effects of oxidation having incorporated therein an antidegradant amount of a compound of Structure I.

Compounds of Structure I can be prepared by reacting:

(a) a compound having the following structure:

$$MS-X-SM' \qquad V$$

wherein M and M' are independently selected from the group consisting of hydrogen and an alkali metal such as sodium or potassium and X is as defined above, with (b) a dual function compound having at least one functional group capable of reacting with a mercaptan or mercaptide and another functional group having antidegradant properties.

The compounds of the present invention are not limited to any particular method of synthesis.

The following commercially available oligomers represent, but do not limit, the compounds of Structure V; Thiokol ® grades LP2, LP3, LP12, LP32 and LP33 as described in Rubber World Magazine's *Blue Book* 1984 Ed., pp. 440–1.

Representative of, but not limited to, the compounds having a dual functionality are compounds of the following structures:

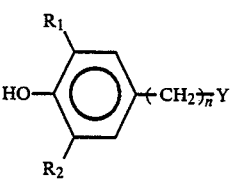

VI and

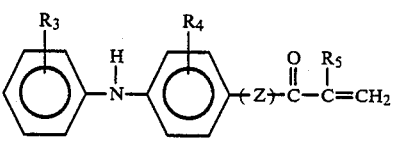

VII wherein $R_1$, $R_2$, $R_3$, $R_4$, $R_5$, n and Z are as defined above and Y is chlorine or bromine. Typical of the compounds conforming to Structures VI and VII are 2,6-di-t-butyl-4-chloromethylphenol and N-[4-(phenylamino)-phenyl]-methacrylamide, respectively.

Preparation of an oligomeric antidegradant using a compound of Structure VI follows the general equation:

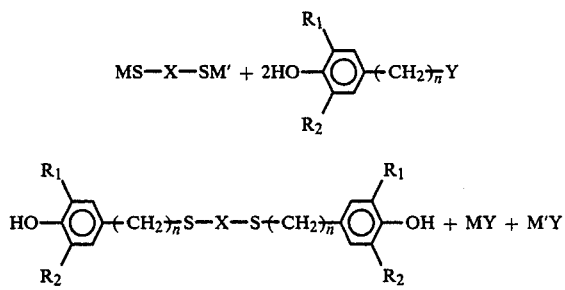

wherein M and M' represent an alkali metal. Similar procedures for preparing small molecule analogs have been described, e.g., see W. Tagaki, "Organic Chemistry of Sulfur", S. Oae, Ed., Plenum Press, New York, 1977, Ch 6. A useful variation involves the use of a two phase (aqueous/organic) solvent system in the presence of a phase transfer catalyst for small molecules as described in W. P. Weber and G. W. Gokel, "Phase Transfer Catalysis in Organic Synthesis", Springer-Verlog, New York, 1977, Ch 13. Example 1 below illustrates the application of a phase transfer technique in the preparation of an oligomeric antidegradant.

Using a compound of Structure VII, the oligomeric antidegradants can be prepared according to the general reaction represented by the equation:

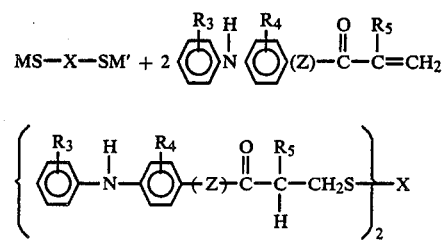

wherein M and $M^1$ represent hydrogen and the resulting mercaptan groups add to the olefin under the influence of a base catalyst or free radical initiation as described for small molecules in the Tagaki reference cited above. Example 2 below illustrates the use of a free radical initiator to effect the synthesis of an oligomeric antidegradant.

All of the oligomeric antidegradants described herein are capable of stabilizing polymers by simple incorporation into the polymer, e.g., by adding to polymer solutions or polymer latices or by addition to the solid polymer, e.g., on a mill or in a Banbury.

Polymers subject to deterioration by oxidation that can be conveniently protected by the oligomeric antidegradants described herein include substituted and unsubstituted, saturated and unsaturated, natural and synthetic polymers. The natural polymers of interest include natural rubber in its various forms, e.g., pale crepe and smoked sheet, balata and gutta percha. The synthetic polymers are polymers prepared from a single monomer (homopolymer) or a mixture of two or more copolymerizable monomers (copolymers) wherein the monomers are combined in a random distribution or block form. The monomers may be substituted or unsubstituted and may possess one or more double bonds, for example, diene monomers, both conjugated and unconjugated, and monoolefins including cyclic and acyclic monoolefins, especially vinyl and vinylidene monomers. Examples of conjugated dienes are 1,3-butadiene, isoprene chloroprene, 2-ethyl-1,3-butadiene, 2,3-dimethyl-1,3-butadiene and piperylene. Examples of nonconjugated dienes are 1,4-pentadiene, 1,4-hexadiene, 1,5-hexadiene, dicyclopentadiene, 1,5-cyclooctadiene and ethylidene norbornene. Examples of acyclic monoolefins are ethylene, propylene, 1-butene, isobutylene, 1-pentene and 1-hexene. Examples of cyclic monoolefins are cyclopentene, cyclohexene, cycloheptene, cyclooctene and 4-methylcyclooctene. Examples of vinyl monomers are styrene, acrylonitrile, acrylic acid, ethylacrylate, butylacrylate, methyl vinyl ether, vinyl acetate, vinyl pyridine, $\alpha$-methylstyrene, methacrylic acid, methyl methacrylate, ethylmethacrylate and glycidylmethacrylate. Examples of vinylidene monomers are vinylidene fluoride and vinylidene chloride. Representative examples of the synthetic polymers used in the practice of this invention are polychloroprene; homopolymers of a conjugated 1,3-diene such as isoprene and butadiene, in particular polyisoprenes having structures configured as cis-1,4; trans 1,4; vinyl 1,2 and vinyl 3,4 addition units or combinations thereof and polybutadienes having cis-1,4; trans 1,4 and vinyl 1,2 addition units or combinations thereof; copolymers of a conjugated 1,3-diene such as isoprene and butadiene with up to 50 percent by weight of at least one copolymerizable monomer including ethylenically unsaturated monomers such as styrene or acrylonitrile; butyl rubber, which is a polymerization product of a major proportion of a monoolefin and a minor proportion of a multiolefin such as butadiene or isoprene; polyurethanes containing carbon to carbon double bonds; and polymers and copolymers of monoolefins containing little or no unsaturation, such as polyethylene, polypropylene, ethylene propylene copolymers and terpolymers of ethylene, propylene and a nonconjugated diene such as dicyclopentadiene, 1,4-hexadiene, ethylidene norbornene and methylene norbornene.

The oligomeric antidegradants of the present invention can be used at a level from about 0.3 to 3.5, preferably 0.5 to 2.5, most preferably 0.5 to 1.5 parts by weight based on the antidegradant portion per 100 parts by weight of polymer. Greater or lesser amounts can be used to constitute an antidegradant amount depending on the susceptibility of the polymer to degradation and the severity of the environment to which the polymer is exposed.

The polymeric compositions to be protected by the oligomeric antidegradants of the present invention can contain any of the conventional compounding ingredients including for example, carbon black, sulfur, processing aids, accelerators, etc.

The following examples are meant to illustrate, not to limit, the practice of the present invention.

EXAMPLE 1

A mixture of 78 g, 2,6-di-t-butyl-4-chloromethyl phenol, 150 g of Thiokol LP-3 (a compound of structure V above wherein M and M' are H and m equals about 5) and 2 g of tetrabutylphosphonium chloride was stirred vigorously in 400 mL toluene and 50 mL water. A solution of 24.5 g of 50% aqueous sodium hydroxide in 50 mL of water was then added at a rate which kept the reaction temperature below 40° C. After stirring 15 minutes subsequent to the addition of the base, the organic phase was washed three times with 500 mL portions of water, dried over Na$_2$SO$_4$ and stripped of toluene on a rotary evaporator. The residue was extracted successively with 1-liter portions of heptane, 2-propanol and methanol, separating the lighter solvent phases by decantation. Evaporation of residual solvent yielded 129 g of a viscous liquid, hereinafter Compound X-1.

EXAMPLE 2

A solution of 40 g Thiokol LP-3, 16.8 g of N-[4-(phenylamino)-phenyl]-methacrylamide and 0.8 g of azobisisobutyronitrile in 60 mL of toluene was stirred overnight at a temperature of 70° C. to 80° C. The product solution was extracted with 300 mL of hexane, two 150 mL portions of 2-propanol and dried to yield 41.8 g of dark viscous liquid, hereinafter Compound X-2.

Compounds X-1 and X-2 were qualitatively characterized by their infrared and proton magnetic resonance spectra to show absorbances derived from the 2,6-di-t-butyl-4-chloromethylphenol and the N-[4-(phenylamino)-phenyl]-methacrylamide, respectively, along with the complete disappearance of the mercaptan band from the Thiokol LP-3.

EXAMPLE 3

Compounds X-1 and X-2 were evaluated in synthetic polyisoprene based polymeric compositions versus a control. The test stocks were formulated according to Table I. Amounts are in parts per 100 parts of polymer.

TABLE I

| Component | Amounts Stock No. | | | | |
|---|---|---|---|---|---|
| | 1 (control) | 2 | 3 | 4 | 5 |
| Synthetic Polyisoprene | 100 | 100 | 100 | 100 | 100 |
| Carbon Black | 50 | 50 | 50 | 50 | 50 |
| Zinc Oxide | 3.0 | 3.0 | 3.0 | 3.0 | 3.0 |
| Stearic Acid | 3.0 | 3.0 | 3.0 | 3.0 | 3.0 |
| Sulfur | 2.0 | 2.0 | 2.0 | 2.0 | 2.0 |
| Accelerator | 1.1 | 1.1 | 1.1 | 1.1 | 1.1 |
| Butylated, Styrenated Cresols | 1.0 | 1.0 | 1.0 | 1.0 | 1.0 |
| Compound X-1 | — | 1.5$^a$ | 3.0$^a$ | — | — |
| Compound X-2 | — | — | — | 1.5$^a$ | 3.0$^a$ |

$^a$Based on contained antidegradant portion.

Specimens of vulcanizate stocks 1–5 were tested on a Monsanto Rheometer, at 135° C., according to ASTM Test Method D2084. Results are shown in Table II.

TABLE II

| Property | Stock Number | | | | |
|---|---|---|---|---|---|
| | 1 | 2 | 3 | 4 | 5 |
| t$_s$2, minutes | 13.0 | 11.5 | 11.7 | 7.7 | 5.5 |
| t$_s$4, minutes | 14.6 | 12.8 | 13.0 | 8.5 | 5.8 |
| t$_c$90, minutes | 34.5 | 36.5 | 37.5 | 32.0 | 31.3 |

EXAMPLE 4

Duplicate specimens of vulcanizate stocks 1, 2 and 4 from Table I were vulcanized for 45 minutes at 135° C. One of the specimens from each stock was extracted with excess acetone (0.96 liters of acetone per 282 g of vulcanized stock), changing to fresh acetone 3 times during 5 days. The extractions were carried out in jars filled to the brim to exclude air.

Physical properties, stress/strain, were tested on both the unextracted and the extracted samples according to ASTM D412. The tests were run on original unaged samples and also on samples which were air oven aged for 24 h at 100° C. Results are shown in Table III.

TABLE III

| Property | Stock Number | | |
|---|---|---|---|
| | 1 | 2 | 4 |
| Original Unextracted | | | |
| Tensile, MPa | 26.6 | 26.6 | 27.0 |
| Elongation, % | 440 | 500 | 500 |
| 300% Modulus, MPa | 17.7 | 14.5 | 16.3 |
| Original Extracted | | | |
| Tensile, MPa | 24.5 | 27.2 | 25.5 |
| Elongation, % | 380 | 485 | 430 |
| 300% Modulus, MPa | 19.0 | 16.5 | 17.9 |
| Aged Unextracted | | | |
| Tensile, MPa | 16.8 | 21.6 | 20.2 |
| Elongation, % | 255 | 350 | 305 |
| 300% Modulus, MPa | — | 18.4 | 20.0 |
| Aged Extracted | | | |
| Tensile, MPa | 8.4 | 17.7 | 18.6 |
| Elongation, % | 180 | 315 | 315 |
| 300% Modulus, MPa | — | 17.4 | 17.6 |

EXAMPLE 5

Duplicate specimens from each of the vulcanizate stocks, 1, 2 and 4 were press cured to a thickness of 0.51 mm for 45 minutes at 135° C. One sample of each was extracted in acetone as described in Example 4. Oxygen absorption tests were performed on the unextracted and extracted samples according to the procedure described in Industrial and Engineering Chemistry, Vol. 43, p. 456 (1951) and Industrial and Engineering Chemistry, Vol. 45, p. 392 (1953). Results are shown in Table IV. Numbers reflect the hours required for the samples to absorb 1% O$_2$ at 100° C.

TABLE IV

| Sample | Stock Number | | |
|---|---|---|---|
| | 1 | 2 | 4 |
| Unextracted | 38 | 40 | 56 |
| Extracted | 10 | 28 | 40 |

While the antidegradants of this invention have been shown to be effective in vulcanized compositions, it is expected that they would be effective in unvulcanized compositions as well.

While certain representative embodiments and details have been shown for the purpose of illustrating the invention, it will be apparent to those skilled in this art that various changes and modifications may be made therein without departing from the scope of the invention.

What is claimed is:

1. A compound having the structure

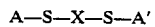

A—S—X—S—A'   I wherein A and A' are radicals independently selected from the group consisting of the following structures:

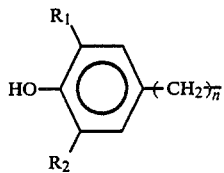

II and

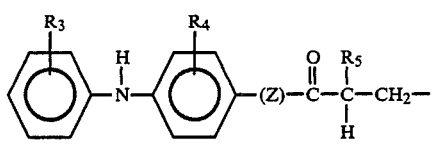

III wherein $R_1$ and $R_2$ are tertiary alkyl radicals having 4 to 8 carbon atoms, n is a whole number of 1 to 8, $R_3$ and $R_4$ are independently selected from the group consisting of hydrogen and alkyl radicals having 1 to 18 carbon atoms, $R_5$ is hydrogen or methyl and Z is —O— or

A' can also be hydrogen; and X is a divalent oligomeric segmer having the structure:

$$+C_2H_4OCH_2OC_2H_4SS\overline{)_m}C_2H_4OCH_2OC_2H_4—$$  IV wherein m ranges from an average of 4 to about 24.

2. The compound according to claim 1 wherein A is a radical of the structure:

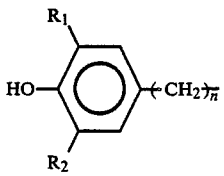

II

3. The compound according to claim 2 wherein $R_1$ and $R_2$ are tertiary butyl and n=1.

4. The compound according to claim 3 wherein A' and A are identical radicals.

5. The compound according to claim 1 wherein A is a radical of the structure:

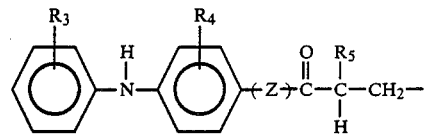

III

6. The compound according to claim 5 wherein $R_3$ and $R_4$ are hydrogen, $R_5$ is methyl and Z is

7. The compound according to claim 6 wherein A' and A are identical radicals.

8. A polymeric composition comprising a polymer susceptible to the degradative effects of oxidation having incorporated therein an effective amount of the compound of claim 1 so as to prevent degradation.

9. A polymeric composition comprising a polymer susceptible to the degradative effects of oxidation having incorporated therein an effective amount of the compound of claim 2 so as to prevent degradation.

10. A polymeric composition comprising a polymer susceptible to the degradative effects of oxidation having incorporated therein an effective amount of the compound of claim 3 so as to prevent degradation.

11. A polymeric composition comprising a polymer susceptible to the degradative effects of oxidation having incorporated therein an effective amount of the compound of claim 4 so as to prevent degradation.

12. A polymeric composition comprising a polymer susceptible to the degradative effects of oxidation having incorporated therein an effective amount of the compound of claim 5 so as to prevent degradation.

13. A polymeric composition comprising a polymer susceptible to the degradative effects of oxidation having incorporated therein an effective amount of the compound of claim 6 so as to prevent degradation.

14. A polymeric composition comprising a polymer susceptible to the degradative effects of oxidation having incorporated therein an effective amount of the compound of claim 7 so as to prevent degradation.

* * * * *

UNITED STATES PATENT AND TRADEMARK OFFICE
CERTIFICATE OF CORRECTION

PATENT NO.   : 4,727,105
DATED        : February 23, 1988
INVENTOR(S)  : Roger J. Hopper It is certified that error appears in the above-identified patent and that said Letters Patent is hereby corrected as shown below:

Title page [21] Appl. No., delete "605035" and insert therefore --695035--.

Signed and Sealed this

Third Day of November, 1992

Attest:

DOUGLAS B. COMER

Attesting Officer

Acting Commissioner of Patents and Trademarks